US00PP34541P2

(12) United States Plant Patent
Krebs

(10) Patent No.: US PP34,541 P2
(45) Date of Patent: Sep. 6, 2022

(54) ***RHODODENDRON* PLANT NAMED 'HOLDENRHODO212'**

(50) Latin Name: *Rhododendron hybrida*
Varietal Denomination: HoldenRhodo212

(71) Applicant: Holden Forests and Gardens, Kirtland, OH (US)

(72) Inventor: Stephen Krebs, Painesville, OH (US)

(73) Assignee: HOLDEN FORESTS AND GARDENS, Kirtland, OH (US)

( * ) Notice: Subject to any disclaimer, the term of this patent is extended or adjusted under 35 U.S.C. 154(b) by 0 days.

(21) Appl. No.: 17/562,221

(22) Filed: Dec. 27, 2021

(51) Int. Cl.
*A01H 6/36* (2018.01)
*A01H 5/00* (2018.01)

(52) U.S. Cl.
USPC ..... Plt./239

(58) Field of Classification Search
USPC ..... Plt./239
See application file for complete search history.

*Primary Examiner* — Annette H Para
(74) *Attorney, Agent, or Firm* — Penny J. Aguirre

(57) ABSTRACT

A new cultivar of hybrid *Rhododendron* plant named 'HoldenRhodo212' that is characterized by its resistance to root rot caused by *Phytophthora cinnamomi*, its old hardiness at least in U.S.D.A Zone 5, its flowers that are fuchsia in color, its adaptability to open field conditions in Northeast Ohio, and its compact form that has been observed after 8 years.

2 Drawing Sheets

Botanical classification: *Rhododendron hybrida.*
Cultivar designation: 'HoldenRhodo212'.

BACKGROUND OF THE INVENTION

The present invention relates to a new and distinct cultivar of *Rhododendron* plant of hybrid origin, botanically known as *Rhododendron* 'HoldenRhodo212' and will be referred to hereafter by its cultivar name, 'HoldenRhodo212'. 'HoldenRhodo212' is a new cultivar of *Rhododendron* shrub grown for use as a landscape plant.

The new cultivar arose from a controlled breeding program by the Inventor in Madison, Ohio and Kirtland, Ohio with the objective of developing new cultivars of *Rhododendron* with resistance to root rot, greater sun adaptability, and compact growth habits.

The new cultivar was derived from a cross made by the Inventor in spring of 1996 between *Rhododendron* 'Rio' (not patented) as the female parent, and *Rhododendron* 'Rocket' (not patented) as the male parent. The Inventor selected 'HoldenRhodo212' as a single unique plant amongst the seedlings that resulted from the above cross in spring of 1998.

Asexual propagation of the new cultivar was first accomplished by semi-hardwood stem cuttings in Madison, Ohio, in 2010 under the direction the Inventor. Asexual propagation by semi-hardwood stem cuttings and tissue culture utilizing meristematic tissue has determined that the characteristics of the new cultivar are stable and are reproduced true to type in successive generations.

SUMMARY OF THE INVENTION

The following traits have been repeatedly observed and represent the characteristics 'HoldenRhodo212'. These attributes in combination distinguish 'HoldenRhodo212' as a new and distinct cultivar of *Rhododendron.*

1. 'HoldenRhodo212' exhibits resistance to root rot caused by *Phytophthora cinnamomi.*
2. 'HoldenRhodo212' exhibits cold hardiness at least in U.S.D.A Zone 5.
3. 'HoldenRhodo212' exhibits flowers that are fuchsia in color.
4. 'HoldenRhodo212' exhibits adaptability to open field conditions in Northeast Ohio.
5. 'HoldenRhodo212' exhibits a compact form that has been observed after 8 years.

The female parent of 'HoldenRhodo212' differs from 'HoldenRhodo212' in having pink flowers with a yellow center and in being susceptible to root rot. The male parent of 'HoldenRhodo212' differs from 'HoldenRhodo212' in having flowers that are rose pink in color and bullate leaves. 'HoldenRhodo212' can also be most closely compared to the *Rhododendron* cultivars 'Besse Howells' (not patented) and 'Haaga' (not patented). 'Besse Howells' is similar to 'HoldenRhodo212' in being cold hardy in U.S.D.A. Zone 5 and in growth rate and habit. 'Besse Howells' differs from 'HoldenRhodo212' in being susceptible to root rot and in having frilled flowers that are darker in color. 'Haaga' is similar to 'HoldenRhodo212' in being cold hardy to U.S.D.A. Zone 5 and in having resistance to root rot when grown in open field conditions with low root rot disease pressure. 'Haaga' differs from 'HoldenRhodo212' in being highly susceptible to root rot when grown under commercial growing conditions and in having lighter pink colored flowers.

BRIEF DESCRIPTION OF THE DRAWINGS

The accompanying color photographs illustrate the overall appearance and distinct characteristics of the new *Rhododendron*. The plant in the photograph is 2.5 years in age as grown outdoors in Kirtland, Ohio.

The photograph in FIG. 1 provides a side view of 'HoldenRhodo212' in bloom.

Figure 1:
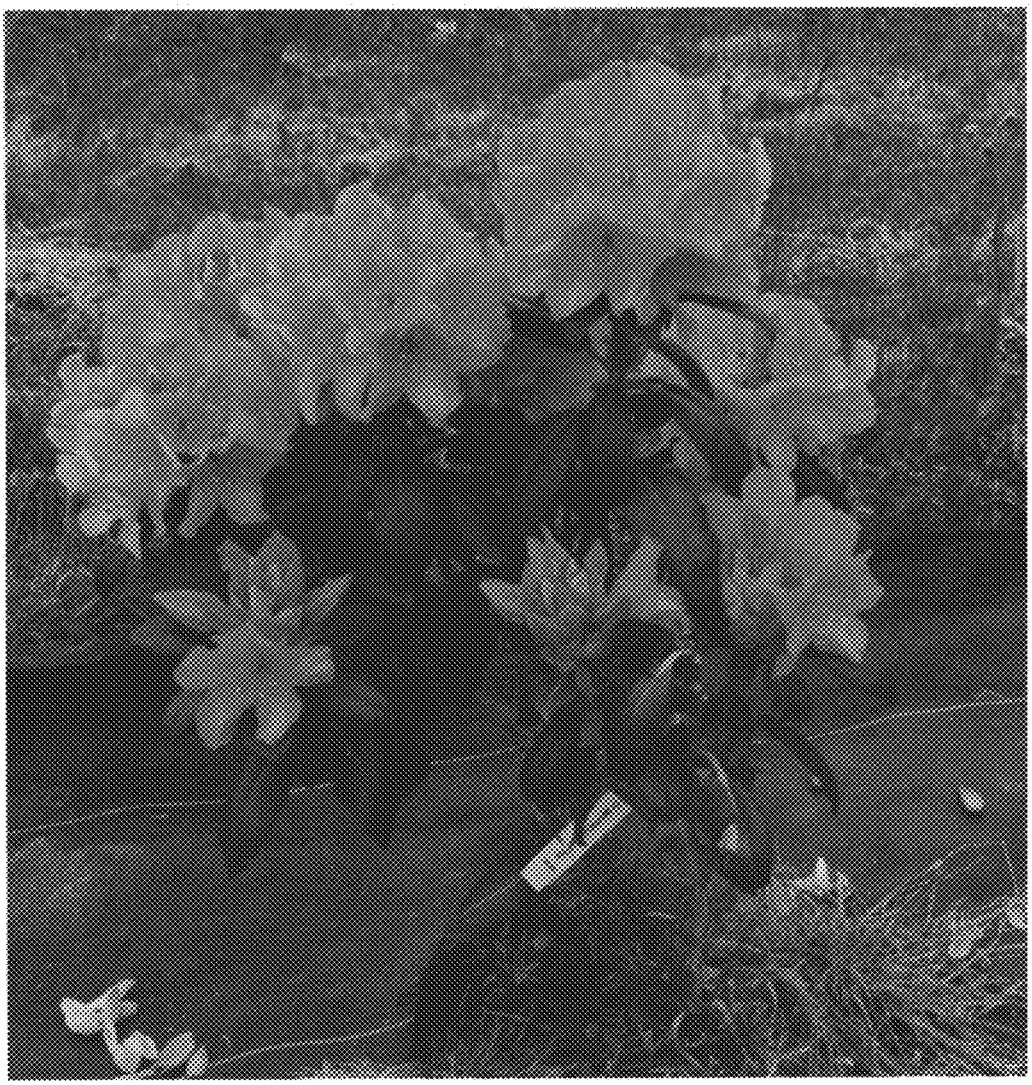
Figure 2:
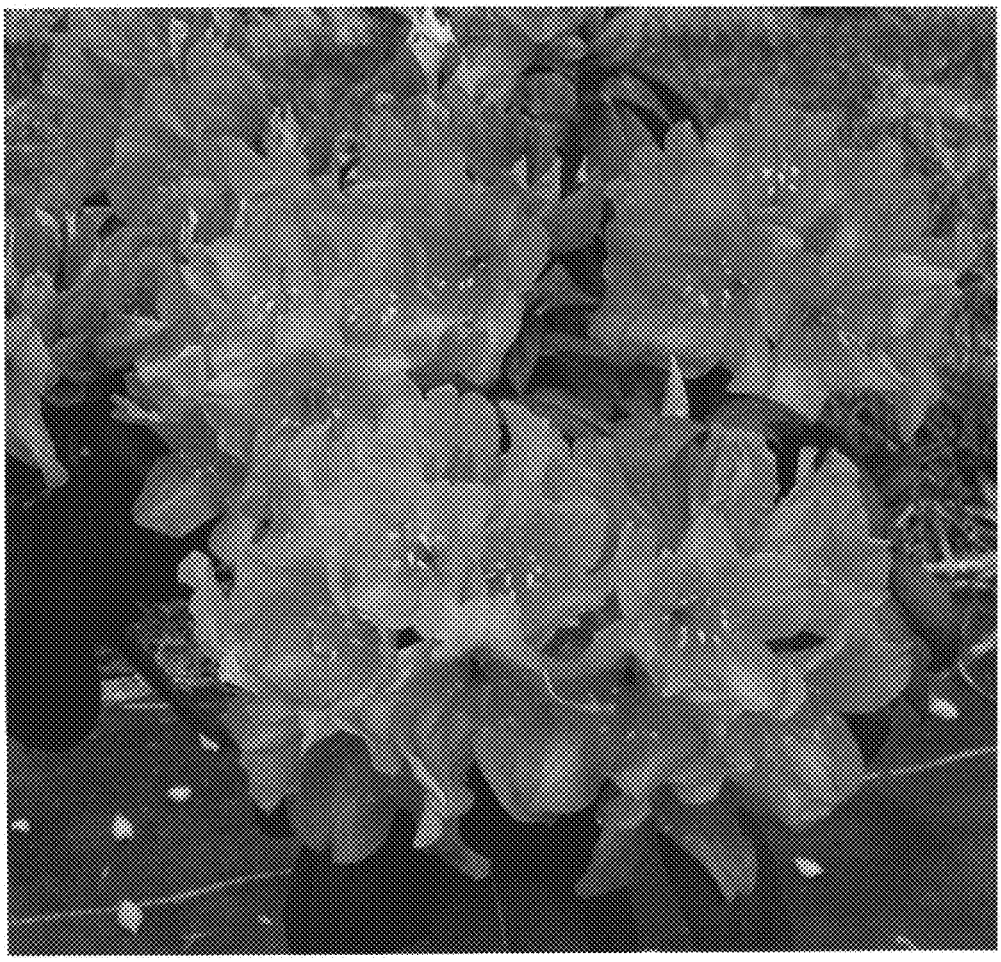

The photograph in FIG. 2 provides a close-up view of the inflorescences of 'HoldenRhodo212'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 8-year-old plants of the new cultivar as grown outdoors in an evaluation garden in Madison, Ohio. The phenotype of the new cultivar may vary with variations in environmental, climatic, and cultural conditions, as it has not been tested under all possible environmental conditions. The color determination is in accordance with The 1995 Colour Chart of The Royal Horticultural Society, London, England, except where general color terms of ordinary dictionary significance are used.

General characteristics:

*Blooming period.*—2 to 3 weeks, depending on weather, typically commencing in late May in Ohio.

*Plant type.*—Evergreen shrub.

*Plant habit.*—Rounded and densely branched.

*Height and spread.*—Reaches 1.1 m in height and 1.2 m in width after 8 years in the landscape.

*Cold hardiness.*—Plant is hardy to at least U.S.D.A. Zone 5a, flower buds are resistant to cold damage when exposed to temperatures of −20 F, possibly colder.

*Diseases and pests.*—Observed to be resistant to root rot caused by *Phytophthora cinnamomi* under field conditions, typical of evergreen *Rhododendrons*; lace bugs (*Stephanitis takeyai*) can establish on leaves under full sun conditions, no other susceptibility or resistance to other pests or diseases has been observed.

*Root description.*—Fibrous, near 165A in color.

*Propagation.*—Tissue culture (preferred) or semi-hardwood stem cuttings.

*Growth rate.*—Moderate.

*Root development.*—4 to 8 weeks for root initiation and 2 years to produce a young plant from a rooted cutting.

Stem description:

*Shape.*—Round.

*Stem color.*—Young; 144A, maturing; late season semi-hardwood stems a blend of 144A and 144B, as the wood lignifies becoming 6A, mature stems; 183B, older stems; 177B and 177C.

*Stem size.*—Main stem; forks at 10 cm in length, 1.5 cm in diameter, lateral branches above fork; 98 cm in length, 2.9 cm in width, current season growth; an average of 6.7 cm in length and 3 mm in width.

*Stem surface.*—Young; slightly rough to the touch, lightly covered in wooly pubescent hairs, becoming less hairy as the stems mature.

*Stem aspect.*—Held outward from main stem.

*Stem strength.*—Strong.

*Branching.*—Densely branched.

Foliage description:

*Leaf shape.*—Elliptic to obovate.

*Leaf division.*—Simple.

*Leaf base.*—Obtuse to rounded.

*Leaf apex.*—Primarily acute.

*Leaf venation.*—Pinnate, upper surface; 138B in color, lateral vein colors ranging from 138B to matching the leaf color, lower surface; midrib and lateral veins 145D and 148C in color.

*Leaf margins.*—Entire.

*Leaf attachment.*—Petiolate.

*Leaf arrangement.*—Alternate, leaf clusters whorled at terminal shoot apex.

*Leaf internode length.*—Up to 1.2 cm.

*Leaf orientation.*—Held mostly upright, some slightly downward.

*Leaf aspect.*—Held mostly flat though can be cupped downward at shoot apex.

*Leaf surface.*—Upper surface: smooth, glabrous, slightly shiny with a thick texture, lower surface: smooth, dull, glabrous.

*Leaf color.*—Young leaves upper surface; 144A with a dark yellow overtone, young leaves lower surface; 144D in color, mature leaves upper surface; a blend of 137C and 138AB, mature leaves lower surface; a blend of 145A and 145B, no change in color in fall.

*Leaf size.*—Ranging from 3.3 to 12.5 cm in length and 2.2 to 4.7 cm in width.

*Leaf quantity.*—An average of 5 leaves per new season shoot and previous season shoot, leaves retained 2 to 3 years.

*Petioles.*—Average of 1.4 mm in length and 2 mm in diameter, near 150B in color, smooth to lightly pubescent surface.

Flower description:

*Inflorescence type.*—Umbellate raceme.

*Lastingness of flowers.*—Total duration of bloom 2 to 3 weeks, flowers petals are self-cleaning.

*Inflorescence size.*—Average of 9.1 cm in height and 9 cm in width.

*Flower size.*—An average of 3.2 cm in depth and 4.5 cm in diameter.

*Flower fragrance.*—None to very faint.

*Flower shape.*—Broad, tubular funnel.

*Flower number.*—Average of 12 per inflorescence.

*Flower aspect.*—Outward.

*Flower bud.*—Obovate in shape, 1; occasionally 2 per terminal shoot whorl, round in cross-section, pointed apex, color; 151B with interior scales closer to 145B, scale edges are near 168B.

*Flower attachment.*—Pedicellate.

*Petal number.*—5.

*Petal shape.*—Ovate to elliptic.

*Petal color.*—Upper and lower surface when opening (balloon stage); 67B, upper surface when fully open; 75D with 75A and 75B (most prominent near apex), lower surface when fully open; 73B, margins 75B.

*Petal surface.*—Waxy, glabrous, and smooth on both upper and lower surfaces.

*Petal margins.*—Entire, slightly undulate.

*Petal apex.*—Acuminate and notched.

*Petal base.*—Fused.

*Petal size.*—An average of 3.5 cm in length and 2.2 cm in width.

*Sepal number.*—5 highly reduced sepals.

*Sepal shape.*—Narrowly deltate.

*Sepal margin.*—Entire.

*Sepal size*.—Average of 1 mm in length and 2 mm in width.

*Sepal surface*.—Pubescent to smooth on upper and lower surface.

*Sepal apex*.—Abruptly rounded.

*Sepal base*.—Fused.

*Sepal color*.—Both surfaces 145B on both immature and mature sepals.

*Peduncle*.—An average of 2.7 cm in height and 4 mm in diameter, near 144B in color, strong, surface slightly to not pubescent.

*Pedicels*.—An average of 2.9 cm in length and 2 mm in diameter, smooth surface, near 144B in color, strong, surface with minimal to no hairs.

Reproductive organs:

*Gynoecium*.—Pistil; 1, stigmas; round in shape, 57A in color, 1 to 2 mm in diameter, style; average 3.6 cm in length, curved, color 58A near stigma fading to 58D near ovary, ovary; 152A in color.

*Androecium*.—Stamens; 10, anthers; oblong to elliptical in shape, 2.5 mm long and 1.5 mm wide, 75A in color; pollen 154D in color and moderate in quantity.

*Fruit/seeds*.—Dehiscent, 5 to 6 valved capsules, size is dependent on pollination, up to 2.3 cm and 1 cm in length and width, color; interior 161B, exterior a mix of 165A, 199C, 200C.

It is claimed:

1. A new and distinct cultivar of *Rhododendron* plant named 'HoldenRhodo212' as herein illustrated and described.

* * * * *